US 6,699,721 B1

(12) United States Patent
Peterson et al.

(10) Patent No.: US 6,699,721 B1
(45) Date of Patent: Mar. 2, 2004

(54) SURFACE COATINGS FOR HOT-MELT ADHESIVE FILM

(75) Inventors: John I. Peterson, Falls Church, VA (US); Tristan Gorrindo, Nashville, TN (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/980,815

(22) PCT Filed: May 9, 2000

(86) PCT No.: PCT/US00/12604
§ 371 (c)(1),
(2), (4) Date: Oct. 23, 2001

(87) PCT Pub. No.: WO00/68662
PCT Pub. Date: Nov. 16, 2000

(51) Int. Cl.[7] ............................. G01N 1/00; G01N 1/18; G01N 21/00; G01N 15/06; C12N 5/02
(52) U.S. Cl. .................. 436/176; 436/174; 436/43; 436/46; 436/47; 436/164; 436/169; 436/178; 435/325; 422/50; 422/58; 422/68.1; 422/55; 422/63; 422/64; 422/65; 422/66; 422/82.05
(58) Field of Search ........................... 422/50, 58, 68.1, 422/55, 63, 64, 65, 66, 82.05; 436/43, 46, 47, 164, 169, 174, 175, 176, 178, 63; 435/325

(56) References Cited

U.S. PATENT DOCUMENTS

| | | | | |
|---|---|---|---|---|
| 5,843,644 A | * | 12/1998 | Liotta et al. | 435/6 |
| 5,843,657 A | * | 12/1998 | Liotta et al. | 435/6 |
| 6,184,973 B1 | * | 2/2001 | Baer et al. | 356/36 |
| 6,251,516 B1 | * | 6/2001 | Bonner et al. | 428/346 |
| 6,528,248 B2 | * | 3/2003 | Lossing et al. | 435/4 |
| 6,531,318 B1 | * | 3/2003 | Palmer-Toy et al. | 436/63 |

FOREIGN PATENT DOCUMENTS

| | | |
|---|---|---|
| WO | WO 97/13838 A | 4/1997 |
| WO | WO 97/13838 * | 4/1997 |
| WO | WO 99/17094 A | 4/1999 |

* cited by examiner

*Primary Examiner*—Jill Warden
*Assistant Examiner*—Brian Sines
(74) *Attorney, Agent, or Firm*—William Michael Hynes; Townsend and Townsend and Crew LLP

(57) ABSTRACT

A low temperature melt film such as EVA is prepared for laser capture microdissection by having a thin specimen non-adhering coating in the range of 0.1% to 10% of the total film thickness placed on the sample exposed side of the film. When the film is brought into contact with the specimen, the specimen non-adhering coating prevents non-specific transfer due to sticky adherence of portions of the sample. At the same time, the non-adhering coating on the low temperature melt film surface can stabilize and protect the low temperature melt film against variations in performance due to ambient humidity and temperature variation. Upon appropriate heating for laser capture microdissection, the barrier of the thin coating allows conventional film melting with otherwise uninhibited adhesion of selected cell areas to the film. Coatings on the low temperature melt film (EVA) surface in selected locations is made by applying film-forming material from a volatile solvent-based solution, followed by evaporation of the solvent. The coating solution can be applied by spraying, dipping, or adding exact volumes to a surface with a micropipet. Spreading a measured volume of solution over the surfaces can coat flat surfaces. The coating thickness can be controlled by the volume and concentration of coating solids added to a known area.

7 Claims, 3 Drawing Sheets

SURFACE COATINGS FOR HOT-MELT ADHESIVE FILM

This invention relates to laser capture microdissection (LCM). More specifically, this disclosure sets forth an improved film for use with laser capture microdissection in which the film is used in contact with the specimen and a coating is provided over the film which prevents non specific transfer of specimen without inhibiting desired laser capture microdissection.

BACKGROUND OF THE INVENTION

Laser capture microdissection (LCM) is known. Specifically, a sample such as a tissue specimen has multiple cell areas scattered throughout. Taking the case of a biopsy for cancer, these cell areas can include cancer cells, pre-cancer cells, irritated cells, normal cells and other tissue. The diagnostician usually desires only one type of cell or cell portion from one cell area—say for purposes of this example—the "pure" cancer cells. Further, the diagnostician requires sufficient quantity of the cells from the selected cell areas to perform further meaningful diagnosis. As a consequence, multiple samples of similar cells from one or more specimens are frequently required.

Laser capture microdissection is preferably performed with a transparent low temperature melting film such as (polyethylene/vinyl acetate), CAS 24937-78-8) (also known as EVA) manufactured by the Du Pont Corporation of Wilmington, Del. The reader will understand that many other manufacturers vend similar materials.

Specifically, a specimen—usually on a glass slide is overlaid with the low temperature melting film such as EVA. Thereafter, a cell area of the sample wanted for dissection is visualized and located, preferably through a microscope. When location has occurred, precision heating and melting of the low temperature film occurs overlying the visualized cell area. The precision heating of the low melting point film occurs by having a laser heat that portion of the low melting point film that overlies the cell area targeted for microdissection. At the precision heated area, flow of the melted EVA occurs from the film to the sample onto the visualized cell area. The sample is adhered to the melted EVA upon solidification of the precision melted portion of the film. Thereafter, the film is removed from the sample, preferably by placing the film overlying the specimen under tension and lifting the film away from the sample. Typically, the sample at the adhered identified cell area sticks to the film with the result that a microdissection occurs. The reader will understand that the film a coating can either be stretched or can reside on a support surface.

In LCM, at least a major part of the mechanism of adhesion is mechanical. The heated film overlying the selected cell area flows into and around the specimen portions to be microdissected. Thereafter, the heated and flowed low temperature melt film solidifies. When the film is withdrawn, the physical interference between the flowed and solidified film material and the cell area of the specimen intended for microdissection causes the film when it is withdrawn to "pull" the selected cell area from the remainder of the specimen. Microdissection occurs.

The primary reason for low temperature in the melting of the film is to avoid damage to or change the nature of the specimen. EVA, among plastics has a uniquely low melting range, which can be controlled by the manufacture. Such manufacture control can include the addition of a variety of ingredients (e.g. rubber) to adjust the melting point and other properties. The ethylene part of the polymer can be used for property variations.

Understanding this mechanical adhesion, the reader can quickly understand the reason for using a low temperature melt film. It is obviously desired to remove the targeted portion of the specimen for further diagnosis. Where the melted film flows in and around the targeted portion of the specimen, undue heating changes the nature of the targeted cellular material and makes may invalidate subsequent analysis or diagnosis. This subsequent analysis, or diagnosis, includes potentially a variety of methods for research and clinical evaluation, such as genetic, immunological, enzymatic, and protein analysis.

At the same time, precise and precision transfer of the intended cell area is required. Such precise transfer must gather only the identified cell area—say for the sake of the example discussed above—the "pure" cancer cells. In the LCM, recovery of materials from cell areas other than cellular material within the identified cell area is referred to as "non-specific transfer." Non specific transfer can be detrimental to further analysis including biological amplification techniques such as PCR. Some applications of LCM are sensitive to very low levels of undesired sample areas.

To avoid non-specific transfer, LCM as currently practiced has divided itself into two broad techniques. In one technique, known as non-contact LCM, the film to which attachment occurs is held spaced a small but constant interval from the sample. When local heating of the EVA or other film utilized occurs, the film expands across the spatial interval, and adheres to the specimen at the visualized portion. When the film is removed, microdissection occurs. A solution to this problem has been to devise various means of spacing the EVA film away from the tissue, so that the EVA contacts the tissue only in the selected spots by its expansion during laser melting.

The EVA expands in a column or pedestal at the area of activation by about 10% to 15%, melts into the tissue sample, and then withdraws away slightly, retaining a microscopic tissue sample upon cooling. The desired spacing of the EVA surface away from the tissue sample is of the order of 10 micrometers. There are various ways of providing the spacing, including putting a spacer film on the EVA, located so the spacer film is in contact with an area of the tissue away from the desired sampling point and holding the EVA surface away from the tissue. With regard to such spacing techniques, non specific transfer may also occur even though a spatial interval is present, due to loose or weakly adhering substances and unevenness of tissue.

It is desirable to press the surface of the EVA against the tissue sample with controlled force, as one of the control parameters of tissue sampling, with the spacing preventing actual contact of the EVA and tissue. The coating of this disclosure may be desirable to prevent non specific transfer in this method also.

It is to be understood that non-contact microdissection is not without problems. Specifically, maintaining the film at a precise closely spaced interval from the specimen at the visualized cell area is difficult. Precision control of the parameters of contact of the low temperature melt film to the sample is difficult.

In another technique of LCM, which is directly applicable to this invention, the film is brought into direct contact with the specimen before melting occurs. In the past, this direct contact with the specimen has caused non-specific transfer. Specifically, the film used—usually EVA—is naturally tacky. This natural tackiness results from the softening point of the film that is required to minimize damage to the microdissected cell area being removed.

Complicating LCM, the biological specimen is also non-homogenous. The specimen typically contains proteins, carbohydrates, fats oils and other cellular materials in an irregular matrix. Portions of this irregular matrix can preferentially adhere to tacky surfaces of the film without the laser heating. Thus, when the targeted material is adhered in the LCM process and withdrawn from the specimen, undesired adjacent cell areas of the specimen are removed and transported by the film. It is this non-specific transfer which it is the purpose of this invention to avoid.

SUMMARY OF THE INVENTION

A low temperature melt film such as EVA is prepared for laser capture microdissection by having a thin specimen non-adhering coating which is hard and non tacky. The hard and non-tacky coating may be in the range of 0.1% to 10% of the total film thickness placed on the sample exposed side of the film. Alternately, a coating may be added to EVA in the range of two to two hundred micro inches. The coating may be applied by any acceptable method including solvent based coatings, laminations and the like. When the coated film is brought into contact with the specimen, the specimen non-adhering coating prevents non-specific transfer due to sticky adherence of portions of the sample. Further, the hard coating will allow use of techniques to remove non-specific transferred material, such as by brushing or washing away attracted material from the hard coating. At the same time, the non-specimen adhering coating on the low temperature melt film surface can stabilize and protect the low temperature melt film against variations in performance due to ambient humidity and temperature variation. Upon appropriate heating for laser capture microdissection, the barrier of the thin coating allows conventional film melting with otherwise uninhibited adhesion of selected cell areas to the film. Coatings on the low temperature melt film (EVA) surfaces in selected locations are made, for example by applying film-forming material from a volatile solvent-based solution, followed by evaporation of the solvent. The coating solution can be applied by spraying, dipping, or adding exact volumes to a surface with a micropipet. Spreading a measured volume of solution over the surfaces can coat surfaces. The volume can control the coating thickness and concentration of coating solids added to a known area.

One of the simplest and most practical ways of making a coating on the EVA surface in selected locations is by applying an appropriate film-forming material from a volatile solvent-based solution followed by evaporation of the solvent. A water or water-ethanol solution is optimal because it does not attack and deform the EVA surface. The usual organic solvent solutions of a polymer are unsuitable because the solvent interacts with the EVA and spoils its surface.

Three materials have been found suitable for this application, although other candidates for water or ethanol solution film formers are possible, including variations of these materials. The EVA used is DuPont Elvax 410. The film materials used are polyvinyl alcohol (Mowiol 40-88 Hoechst, mw 127,000, Aldrich Chemical Co. 32,459-0, CAS 9002-29-5), polyvinylpyrrolidone (PVP, Fisher Scientific Co. BP431-100, mw 40,000, CAS 9003-39-8), and chitosan (Aldrich Chemical Co. 44,887-7, medium mw, CAS 9012-76-4). These are used in solution in water or 50% ethanol in water at concentrations from 0.1 g/100 ml to 10 g/100 ml, most commonly 1 g/100 ml. The chitosan solutions contain 5% by volume acetic acid in the water to solubilize the chitosan.

To apply the coatings evenly it may be necessary to prepare the surface of the EVA by plasma etching to make it solution wettable. Also, some coating materials, particularly PVP, require etching of EVA to give satisfactory film adhesion. Exposure for about one minute to a plasma in air at a pressure of approximately one-half torr is sufficient. The articles to be treated are placed in a six-inch diameter glass vacuum desiccator with internal electrodes, connected to a vacuum leak-testing probe as a high-voltage high-frequency current source.

The coating solution can be applied by spraying, dipping, or adding exact volumes to a surface with a micropipet. Applying a measured volume of solution of known concentration over known surface area, as on caps, can control the film thickness added to the known area.

It has also been proposed to accomplish laser capture microdissection utilizing a conical surface. In this application, successive application and rotation of a conical surface enables a high concentration of similar cells at closely spaced intervals over the flat surface. Utilizing this disclosure, rod shapes can be coated completely.

It has also been proposed to provide such rods with spacer bands. These spacer bands contact the specimen or slide surface and hold the low temperature melt film a given distance away from the specimen. Such spacer bands can be protected against non-specific transfer with the coatings set forth herein. Dipping, with rotation to improve evenness of coating application may be used to evenly coat the spacer bands. Rods can also be coated by addition of solution from a micropipet during rotation.

Pattern coating, or control of the area coated by a film can be done by masking during the plasma etching process so that the non etched surface of EVA is not wetted by the solution. Various methods of printing transfer of solution to the surface can also be used to apply the solutions to coat the EVA in selected regions. Addition of ethanol to the solution of coating material will vary the wettability of the solution on the EVA.

The thickness of the film can be estimated by calculation from the volume and concentration added to a known area. The thickness of the film can also be measured microscopically by counting interference fringes with the film against a glass slide surface or by measuring the focus location change when focusing on the upper and lower surface of a film. Inclusion of a dye, preferably fluorescent, in the film can be used to calibrate the thickness by color intensity measurement. A dye also makes it easy to see the location of the film, which would otherwise be difficult. An example dye is rhodamine B (CAS 81-88-9) in a concentration of 100 micrograms/ml in the solution.

BRIEF DESCRIPTION OF THE DRAWINGS

FIG. 5 illustrates in side elevation section the coating of this invention applied to a spacer band; and, FIG. 6 illustrates a pattern prepared surface coated in a pattern with the coating of this invention, the pattern prepared surface being ideal for flat films, especially tapes and the like.

DESCRIPTION OF THE SPECIFIC EMBODIMENTS

Figure 1:
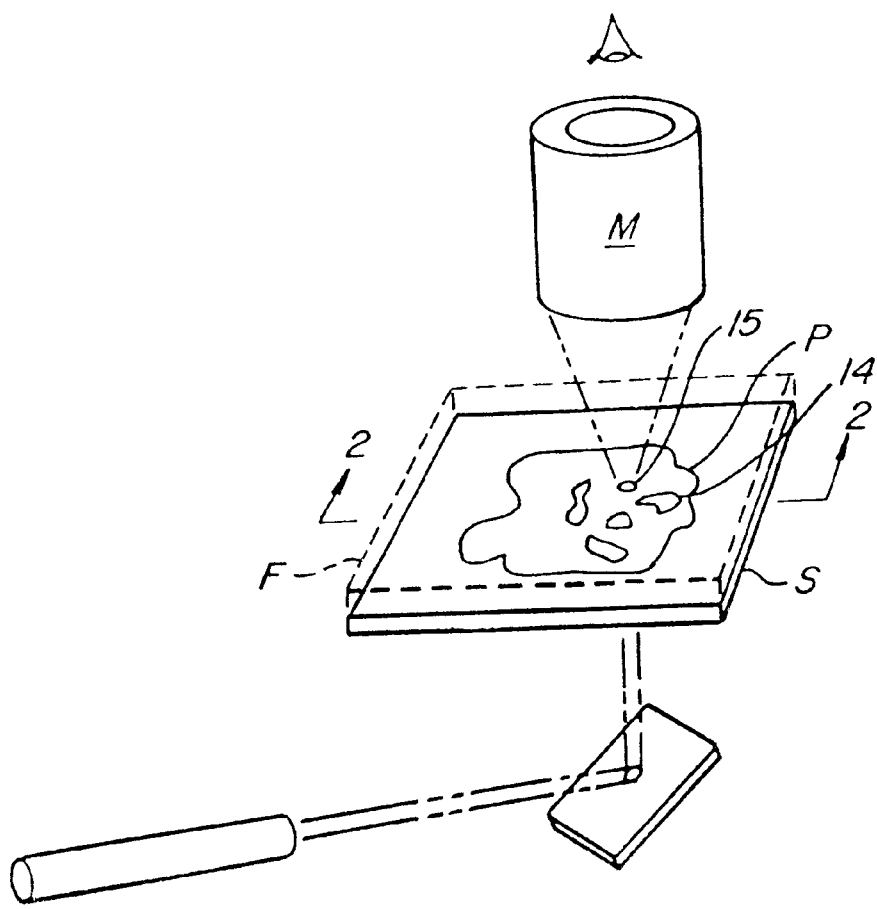
FIG. 1 is a view of conventional laser capture microdissection illustrating a slide mounted specimen covered with a low temperature melt film having a cell area visualized for microdissection and illustrating schematically the laser path for heating and adhering the film to the cell area of the specimen.

Referring to FIG. 1, eye E observes through microscope M slide S having specimen P. Schematically shown on slide S at specimen P is two types of target cell areas, 14–15. Those have familiarity with some biopsies will understand that cells are found in a matrix in such samples. Here we schematically illustrate the cells of interest as target cell area 15. The reader will understand that eye E is schematic; present practice includes the use of digital displays and the like.

We schematically show a microscope configuration. More particularly, we illustrate schematically laser L deflected by mirror 20 upward through slide S and specimen P.

Most importantly, low temperature melt film F immediately overlies specimen P. It is this film which is locally and precision heated by laser L. When such heating occurs, precision melting of low temperature melt film F occurs and microdissection of specimen P at target cell area 15 can occur. Sequentially, light from laser L couples to low temperature melt film F and causes melting. Thereafter, molten low temperature melt film F attaches to specimen P. When the film is removed, the attached target cell area 15 is removed with the film.

Figure 2:
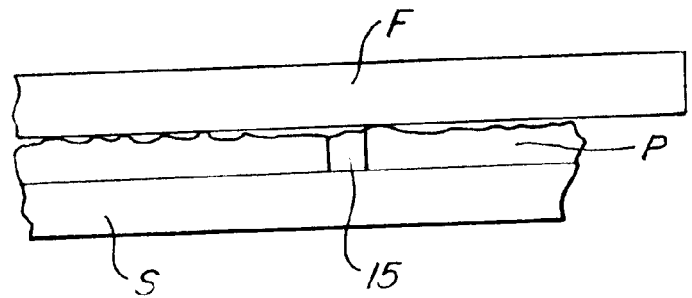
FIG. 2 is an enlarged cross section illustrating the sample, the film, and the coating between the film and sample, a portion of the film shown melted and expanding through the coating to form normal laser capture microdissection.

Observing FIG. 2 taken along section lines 2—2 of FIG. 1, a side elevation view is taken at the sample. It is clearly seen that the film is in contact with the sample. There has been an effort to schematically represent the irregular top 18 of specimen P.

Figure 3:
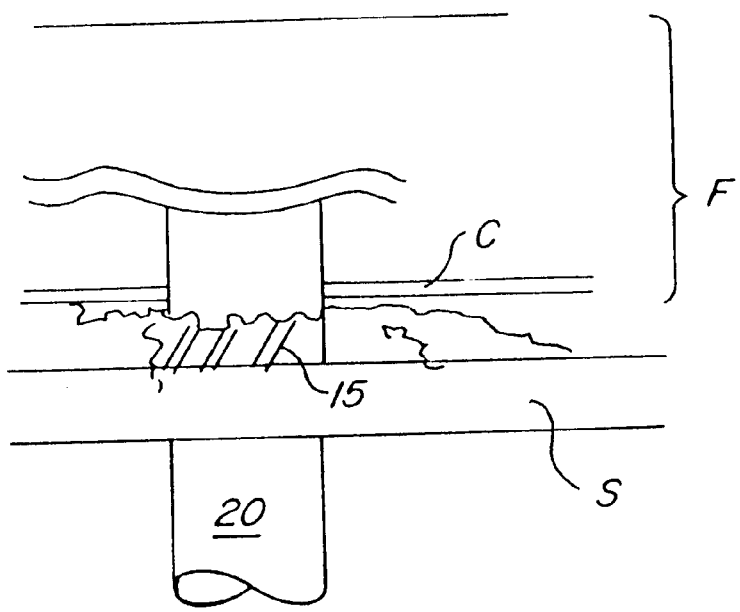
FIG. 3 is a further enlarged section of the film illustrating the molten portion of the film breaking through coating of this invention and adhering to the specimen at least through some mechanical attachment.

Turning to FIG. 3, a further enlarged view of the LCM is shown. Low temperature melt film F is shown having the non-adhering coating C of this invention attached. Beam 20 from laser L is shown passing upward through slide S, specimen P, and coupling to low temperature melt film F. As a result, molten column 25 passes through non-adhering coating C and allows molten columns 25 to adhere to specimen P at cell area 15. When low temperature melt film F is raised from specimen P, microdissection occurs.

We have already given the composition of non-adhering coating C on low temperature melt film F. Some attention can be directed here to the thickness of non-adhering coating C. Typically, and on a broad range, non-adhering coating C is between 0.1% and 5% of the total thickness of low temperature melt film F. In a narrow range, such thickness is from 3% to 0.5% with optimum thickness being the range of 1%.

The reader will also understand that the coating can be limited in terms of coating thickness. Such coating thickness can nominally be 1 micron in a narrow range, 0.5 to 5 microns in an intermediate range, and 0.1 to 10 microns in a broad range. Given that fact that films may vary widely in total thickness, the limitations on coating thickness are preferred.

Low temperature melt film F nominally is in the range of 100 microns thick, although total thickness of the film may vary. It is to be understood that low temperature melt film F is capable of transmitting all (tensile) forces necessary for the microdissection. Non-adhering coating C does not appreciably contribute to such tensile forces.

In one embodiment of this invention, non-adhering coating C is of chitosan and as a consequence very brittle. A coating which breaks away sharply from the EVA wetted LCM spot is important, so that a sharp edge or departure zone is maintained between the film heated to become adhesive and the surrounding non-activated film which is coated against the non-specific transfer. All that is required is that non-adhering coating C is sufficiently non-adhering to specimen P so that non-specific transfer does not occur.

In what follows are specific examples of film and film coating, which we have used:

| Example | Coating | Eva Film | Solution | EVA Treatment | Thickness |
|---|---|---|---|---|---|
| 1 | polvinylpyrrolidone (PVP, Fisher Scientific Co. BP431-100, mw 40,000, CAS 9003-39-8)\on DuPont Elvax 410 | 1% polyvinyl-pyrrolidone, | 50% ethanol in water | plasma etch | 0.3 micrometers |
| 2 | polyvinylpyrrolidone (PVP, Fisher Scientific Co. BP431-100, mw 40,000, CAS 9003-39-8)\on DuPont Elvax 410 | 1% polyvinyl-pyrrolidone in water | | plasma etch | 0.3 micrometers |
| 3 | polyvinyl alcohol (Mowiol 40-88 Hoechst, mw 127,000, Aldrich Chemical Co. 32) 459-0, CAS 9002-89-5) on DuPont Elvax 410 | 5% Mowiol, | 50% ethanol in water | | 10 micrometers |
| 4 | chitosan (Aldrich Chemical Co. 44,886-7, medium mw, CAS 9012-76-4) on DuPont Elvax 410 | 1% chitosan | 5% acetic acid, 50% ethanol in water | plasma etch | 0.1 micrometer |

We have shown the coating here applied to a film surface. It will be just as apparent that application could as well be to a cylindrical surface such as conical surface 30 on rod R.

Figure 4:
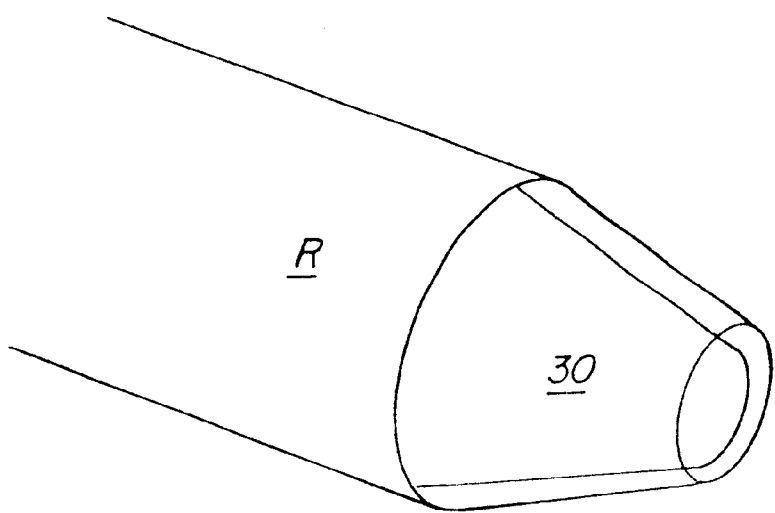
FIG. 4 illustrates in side elevation section the coating of this invention applied to a cylindrical surface.

In this case, low temperature melt film F' is applied around rod R of FIG. 4 having non-adhering coating C'.

Figure 5:
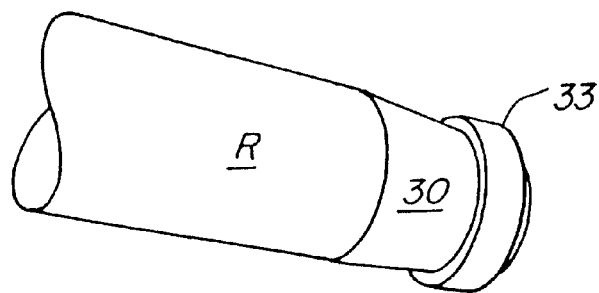
Figure 6:
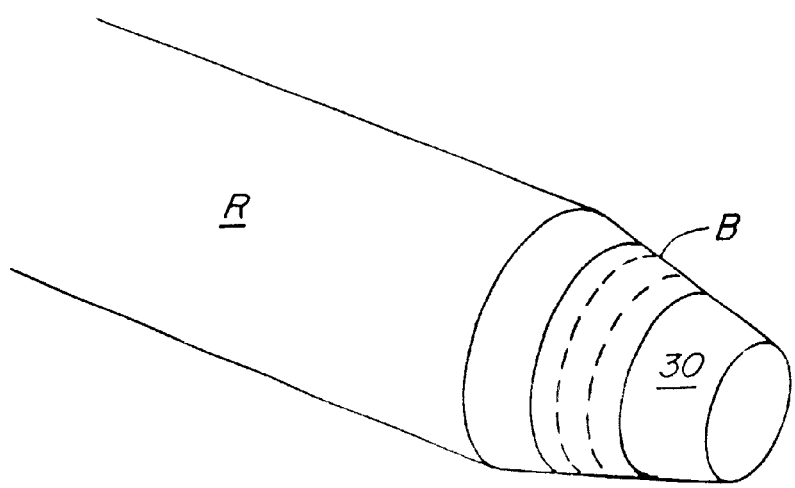

With respect to FIG. 5, non-adhering coating C is used on conical surface 30 having rimmed 33. Rim 33 with non-adhering coating C thereon prevents non-specific transfer.

Finally, and with respect to FIG. 5, low temperature melt film F has been exposed to plasma at band B. Such exposure enables band B to be wettable. When wetted with the solutions set forth in the examples above, non-adhering coating C appears as a band about conical surface 30.

The reader will understand that the foregoing specification is exemplary. We show a single coating. The coating could be a laminate, or even multiple coatings. Further, from what has been previously addressed, the most important aspect of this invention is the use of the hard coating over the convention film, such as EVA. The method or material used for the coating may widely vary.

What is claimed is:

1. In the process of laser capture microdissection including:

providing a specimen having a matrix of cells for examination;

providing a low temperature melt film for laser capture microdissection;

overlaying and contacting the specimen with the low temperature melt film;

visualizing the specimen to determine a cell area in the matrix of cells for microdissection;

heating the film with a laser overlying the cell area to cause the film to melt and locally adhered to the cell area;

removing the film from the specimen to cause a locally adhered cell area to be removed with the film;

the improvement comprising the step of:

placing a specimen non adhering coating on the low temperature melt film, the specimen non adhering coating exposed to and in contact with the sample, the coating being between 0.1% and 5% of the total thickness of the film whereby when the heating of the film overlying the cell area causes melting of the film to occur, melting occurs through the specimen non adhering coating.

2. In the process of laser capture microdissection according to claim 1 and where the improvement includes:

the coating being between 0.1 microns and 10 microns thick.

3. In the process of laser capture microdissection according to claim 1 and wherein the improvement includes:

the placed specimen non adhering coating is selected from the group consisting of polyvinyl alcohol, polyvinylpyrrolidone, and chitosan.

4. In the process of laser capture microdissection according to claim 1 and where the improvement includes:

the placed specimen non adhering coating is in a solution.

5. In the process of laser capture microdissection according to claim 4 and where in the solution comprises water and ethanol and concentration from the 0.1–10 ge/100 ml.

6. In the process of laser capture microdissection according to claim 4 and wherein the improvement includes:

the water and ethanol solution includes 50:50 ethanol:water.

7. In the process of laser capture microdissection according to claim 2 and where the improvement includes:

treating the low temperature melting point film by plasma etching to permit wetting of the film prior to applying the coating.

* * * * *